(12) United States Patent
Salvadori et al.

(10) Patent No.: US 7,645,968 B2
(45) Date of Patent: Jan. 12, 2010

(54) METHOD FOR SECURING A URINE METER TO A URINE BAG

(75) Inventors: Lawrence Salvadori, San Diego, CA (US); Dennis Schreuer, Lemon Grove, CA (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 11/478,749

(22) Filed: Jun. 30, 2006

(65) Prior Publication Data
US 2008/0009813 A1    Jan. 10, 2008

(51) Int. Cl.
*H05B 6/67* (2006.01)
*A61M 1/00* (2006.01)

(52) U.S. Cl. ............... 219/769; 219/633; 219/764; 219/765; 219/770; 156/379; 156/385; 156/401; 156/272.2; 156/275.1; 600/548; 600/573; 600/575; 600/580; 600/581; 604/317; 604/318; 604/265; 604/326; 604/323

(58) Field of Classification Search ............... 219/769, 219/633, 635, 764, 765, 770; 156/379, 385, 156/401, 272.2, 275.1; 600/548, 573, 575.5, 600/575, 580, 581; 604/318, 317, 265, 326, 604/323, 544, 350
See application file for complete search history.

(56) References Cited

U.S. PATENT DOCUMENTS

| | | |
|---|---|---|
| 693,127 A | 2/1902 | Gardner et al. |
| 1,951,196 A | 3/1934 | Medows et al. |
| 2,630,303 A | 3/1953 | Krucker |
| 3,259,920 A | 7/1966 | Voller |
| 3,312,221 A | 4/1967 | Overment |
| 3,529,599 A | 9/1970 | Folkman et al. |
| 3,534,738 A | 10/1970 | Huck |
| 3,537,109 A | 11/1970 | Spurrier et al. |
| 3,537,455 A | 11/1970 | Skyles et al. |
| 3,583,401 A | 6/1971 | Vailiancourt |
| 3,601,119 A | 8/1971 | Engelsher |
| 3,650,272 A | 3/1972 | Ericson |
| 3,661,143 A | 5/1972 | Henkin |
| 3,661,153 A | 5/1972 | Polk et al. |
| 3,683,894 A | 8/1972 | Villari |

(Continued)

FOREIGN PATENT DOCUMENTS

| GB | 2322079 | 8/1998 |
|---|---|---|
| WO | WO95/13016 | 5/1995 |

OTHER PUBLICATIONS

Chilean Office Action—Application No. 1879-2007 dated Feb. 6, 2009.

*Primary Examiner*—Shawntina Fuqua
(74) *Attorney, Agent, or Firm*—Lawrence A. Chaletsky, Esq (57) ABSTRACT

A method is provided for securing a fluid meter to a fluid collection bag. The method includes the steps of providing a meter ha6 ving a housing defining a fluid receptacle and at least one drain opening, providing a collection bag defining a fluid reservoir and having at least one inlet opening and securing the meter to the bag using an RF welding device to allow fluid communication between the fluid receptacle and the fluid reservoir. In one embodiment, the housing includes a raised surface positioned about the at least one drain opening to which the collection bag is welded.

10 Claims, 6 Drawing Sheets

U.S. PATENT DOCUMENTS

| | | |
|---|---|---|
| 3,699,964 A | 10/1972 | Ericson |
| 3,716,055 A | 2/1973 | Schultze |
| 3,776,231 A | 12/1973 | Holbrook et al. |
| 3,800,795 A | 4/1974 | Walker |
| 3,820,546 A | 6/1974 | Chittenden et al. |
| 3,831,453 A | 8/1974 | McWhorter |
| 3,838,691 A | 10/1974 | Paludan et al. |
| 3,888,236 A | 6/1975 | Marx |
| 3,896,718 A | 7/1975 | Giambalvo |
| 3,906,930 A | 9/1975 | Raia et al. |
| 3,943,929 A | 3/1976 | Patel |
| 3,952,729 A | 4/1976 | Libman et al. |
| 3,961,529 A | 6/1976 | Hanifl |
| 4,000,649 A | 1/1977 | Hanifl |
| 4,002,075 A | 1/1977 | Cross |
| 4,013,064 A | 3/1977 | Patel et al. |
| 4,014,322 A | 3/1977 | Shah |
| 4,015,605 A | 4/1977 | McWhorter |
| 4,019,707 A | 4/1977 | Quinn et al. |
| 4,027,842 A | 6/1977 | Mittleman |
| 4,055,187 A | 10/1977 | Patel et al. |
| 4,085,616 A | 4/1978 | Patel et al. |
| 4,085,755 A | 4/1978 | Burrage |
| 4,095,589 A | 6/1978 | Manschot et al. |
| 4,100,802 A | 7/1978 | Layton |
| 4,105,500 A | 8/1978 | Libman et al. |
| 4,106,675 A | 8/1978 | Taylor |
| 4,109,837 A | 8/1978 | Taylor |
| 4,131,016 A | 12/1978 | Layton |
| 4,176,412 A | 12/1979 | Peterson |
| 4,178,934 A | 12/1979 | Forman |
| 4,187,722 A | 2/1980 | Layton |
| 4,189,789 A | 2/1980 | Hofstetter |
| 4,192,295 A | 3/1980 | Sherlock |
| 4,200,112 A | 4/1980 | McWhorter |
| 4,219,177 A | 8/1980 | O'Day |
| 4,238,448 A | 12/1980 | Salvador et al. |
| 4,241,017 A | 12/1980 | Balistreri |
| 4,254,771 A | 3/1981 | Vidal |
| 4,265,243 A | 5/1981 | Taylor |
| 4,280,498 A | 7/1981 | Jensen |
| 4,301,813 A | 11/1981 | Merry et al. |
| 4,305,290 A | 12/1981 | Taylor |
| 4,305,403 A | 12/1981 | Dunn |
| 4,305,404 A | 12/1981 | Dunn |
| 4,305,405 A * | 12/1981 | Meisch ........................ 600/575 |
| 4,312,351 A | 1/1982 | Kurtz et al. |
| 4,312,352 A | 1/1982 | Meisch et al. |
| 4,313,447 A | 2/1982 | Peterson et al. |
| 4,317,550 A | 3/1982 | Hannah |
| 4,328,828 A | 5/1982 | Cianci |
| 4,332,252 A | 6/1982 | Taylor |
| 4,333,480 A | 6/1982 | Villari et al. |
| 4,334,537 A | 6/1982 | Peterson |
| 4,344,432 A | 8/1982 | Pankau |
| 4,366,836 A | 1/1983 | Villari |
| 4,372,313 A | 2/1983 | Villari et al. |
| 4,384,485 A | 5/1983 | Layton et al. |
| 4,386,930 A | 6/1983 | Cianci |
| 4,393,880 A | 7/1983 | Taylor |
| 4,417,891 A | 11/1983 | Cianci |
| 4,417,892 A | 11/1983 | Meisch |
| 4,421,509 A | 12/1983 | Schneider et al. |
| 4,436,024 A | 3/1984 | Arden et al. |
| 4,447,939 A | 5/1984 | Taylor |
| 4,449,969 A | 5/1984 | Schweizer |
| 4,450,936 A | 5/1984 | Strom |
| 4,452,253 A | 6/1984 | Peterson et al. |
| 4,460,362 A | 7/1984 | Bates |
| 4,462,510 A | 7/1984 | Steer et al. |
| 4,465,479 A | 8/1984 | Melsch |
| 4,465,484 A | 8/1984 | Cianci |
| 4,475,907 A | 10/1984 | Voges |
| 4,483,688 A | 11/1984 | Akiyama |
| 4,490,144 A | 12/1984 | Steigerwald |
| 4,501,584 A | 2/1985 | Cianci et al. |
| 4,503,864 A | 3/1985 | Powers |
| 4,511,357 A | 4/1985 | Steigerwald |
| 4,511,358 A | 4/1985 | Johnson, Jr. et al. |
| 4,512,770 A | 4/1985 | Cianci et al. |
| 4,521,213 A | 6/1985 | Steigerwald |
| 4,526,576 A | 7/1985 | Cianci |
| 4,529,398 A | 7/1985 | Wong et al. |
| 4,534,766 A | 8/1985 | Steer et al. |
| 4,551,141 A | 11/1985 | McNeil |
| 4,562,984 A | 1/1986 | Sherlock et al. |
| 4,564,361 A | 1/1986 | Akiyama |
| 4,573,983 A | 3/1986 | Annis |
| 4,579,126 A | 4/1986 | Cianci |
| 4,581,763 A | 4/1986 | Olsen |
| 4,604,092 A | 8/1986 | Silver |
| 4,604,095 A | 8/1986 | Samuelsen |
| 4,606,420 A | 8/1986 | Silver |
| 4,606,736 A | 8/1986 | Van De Weghe |
| 4,619,648 A | 10/1986 | Rath et al. |
| 4,622,981 A | 11/1986 | Sherlock |
| 4,625,734 A | 12/1986 | Sherlock et al. |
| 4,631,056 A | 12/1986 | Dye |
| 4,633,887 A | 1/1987 | Edwards et al. |
| 4,634,437 A | 1/1987 | Lowthain |
| 4,640,128 A | 2/1987 | Lewis |
| 4,642,105 A | 2/1987 | Toter |
| 4,650,478 A | 3/1987 | Dunn |
| 4,658,834 A | 4/1987 | Blankenship et al. |
| 4,659,329 A | 4/1987 | Annis |
| 4,661,100 A | 4/1987 | Rechsteiner |
| 4,691,557 A | 9/1987 | Dunn et al. |
| 4,693,707 A | 9/1987 | Dye |
| 4,693,712 A | 9/1987 | Bates |
| 4,699,155 A | 10/1987 | Villari et al. |
| 4,700,714 A | 10/1987 | Fuisz |
| 4,702,740 A | 10/1987 | Bates |
| 4,717,388 A | 1/1988 | Steer et al. |
| 4,723,944 A | 2/1988 | Jensen |
| 4,723,950 A | 2/1988 | Lee |
| 4,728,324 A | 3/1988 | Steigerwald et al. |
| 4,731,062 A | 3/1988 | Gross et al. |
| 4,738,671 A | 4/1988 | Elliott et al. |
| 4,743,236 A | 5/1988 | Manschot |
| 4,745,929 A | 5/1988 | Silver |
| 4,753,249 A | 6/1988 | Muller |
| 4,790,837 A | 12/1988 | Gross et al. |
| 4,804,376 A | 2/1989 | Layton |
| 4,815,477 A | 3/1989 | McWhorte et al. |
| 4,838,876 A | 6/1989 | Wong et al. |
| 4,850,375 A | 7/1989 | Rosenburg |
| D303,714 S | 9/1989 | Manschot |
| 4,865,046 A | 9/1989 | Duran |
| 4,909,478 A | 3/1990 | Steer |
| 4,911,697 A | 3/1990 | Kerwin |
| 4,913,161 A | 4/1990 | Villari et al. |
| 4,936,837 A | 6/1990 | Wexler et al. |
| 4,946,451 A | 8/1990 | Cianci |
| 4,955,879 A | 9/1990 | Mervine |
| 4,972,844 A | 11/1990 | Cianci et al. |
| 5,026,359 A | 6/1991 | Burroughs |
| 5,098,418 A | 3/1992 | Maitz et al. |
| 5,116,139 A | 5/1992 | Young et al. |
| 5,119,675 A | 6/1992 | Mohiuddin |
| 5,160,329 A | 11/1992 | Oxley |
| 5,207,661 A | 5/1993 | Repschlager |
| 5,211,642 A | 5/1993 | Clendenning |
| 5,217,443 A | 6/1993 | Oxley |
| 5,300,050 A | 4/1994 | Everett, Jr. et al. |

| | | | | | |
|---|---|---|---|---|---|
| 5,312,379 A | 5/1994 | Rahe | 5,961,501 A | 10/1999 | Cassidy et al. |
| 5,354,132 A | 10/1994 | Young et al. | 5,989,234 A | 11/1999 | Valerio et al. |
| 5,356,398 A | 10/1994 | Willis | 6,129,684 A | 10/2000 | Sippel et al. |
| 5,368,583 A | 11/1994 | Fleury | 6,129,714 A | 10/2000 | Kocsi |
| 5,409,014 A | 4/1995 | Napoli et al. | 6,210,383 B1 | 4/2001 | Want et al. |
| 5,417,657 A | 5/1995 | Hauer | 6,250,482 B1 | 6/2001 | Want et al. |
| 5,423,792 A | 6/1995 | Oxley | 6,338,728 B1 | 1/2002 | Valerio |
| 5,429,624 A * | 7/1995 | Coelho, Jr. .................. 604/323 | 6,409,131 B1 | 6/2002 | Bently et al. |
| 5,439,456 A | 8/1995 | Fabricant | 6,409,971 B1 | 6/2002 | Wilkinson et al. |
| 5,466,229 A | 11/1995 | Elson et al. | 6,551,292 B1 | 4/2003 | D'Acchioli et al. |
| 5,489,281 A | 2/1996 | Watanabe et al. | 6,582,379 B1 | 6/2003 | Stisen |
| 5,507,734 A | 4/1996 | Everett, Jr. et al. | 6,635,036 B1 | 10/2003 | Tanghoej et al. |
| 5,523,055 A | 6/1996 | Hansen et al. | 6,736,803 B2 | 5/2004 | Cawood |
| 5,569,225 A | 10/1996 | Fleury | 6,793,651 B1 | 9/2004 | Bennett et al. |
| 5,616,138 A | 4/1997 | Propp | D496,993 S | 10/2004 | Kubalack et al. |
| 5,662,630 A | 9/1997 | Raynie | D497,205 S | 10/2004 | Kubalack et al. |
| 5,725,515 A | 3/1998 | Propp | 2002/0002363 A1* | 1/2002 | Urakawa et al. ............ 604/544 |
| 5,792,127 A | 8/1998 | Marran | 2007/0203464 A1* | 8/2007 | Green et al. ................ 604/323 |
| 5,891,051 A | 4/1999 | Han et al. | 2007/0213639 A1* | 9/2007 | Salvadori et al. ............ 600/584 |
| 5,919,146 A | 7/1999 | Propp | | | |

* cited by examiner

METHOD FOR SECURING A URINE METER TO A URINE BAG

BACKGROUND

1. Technical Field

The present disclosure relates to a fluid collection system including a fluid collection bag and a fluid meter. More specifically, the present disclosure relates to a method for securing a fluid collection meter to a fluid collection bag.

2. Background of Related Art

Urine collection systems including a urine collection meter attached to a urine collection bag are well known and are commonly used to collect urine from a catheterized patient. Typically, a urine meter is attached to a urine collection bag and includes one or more drain openings positioned at an upper end of the meter which communicate with openings in the collection bag. A drain tube having a first end connected to a catheterized patient has a second end which empties into the urine meter. The urine meter includes at least one fluid receptacle and a faceplate including indicia for indicating the volume of fluid within the fluid receptacle.

In use, after a predetermined period of catheterization, the output volume of urine can be recorded by medical personnel and the urine collected in the meter can be emptied into the urine collection bag by tilting the urine meter. When the urine meter is tilted, urine in the fluid receptacle flows from the bottom portion of the urine meter to an upper portion of the urine meter where it travels through the drain opening or openings into the urine collection bag.

Generally, a urine meter is secured to a urine bag by securing the area of the meter about the drain opening or openings to a urine collection bag. Prior to or subsequent to this bonding step, an opening is formed in the collection bag in communication with the drain opening or openings. The entire assembly can be hung on a support structure, e.g., a hospital bed, by a support hangar which is secured to the collection bag. The urine meter must be securely bonded to the collection bag to prevent urine leakage.

Several methods are known for securing a urine meter to a urine bag. For example, in one known method, docking structure is secured to a collection bag and the docking structure is subsequently secured to the urine meter such as by solvent bonding or using adhesives. Such methods, although somewhat effective, result in increased manufacturing expense and an enlarged bag profile.

Accordingly, it would be desirable to provide a method for securing a urine meter to a urine collection bag which is inexpensive, results in a reduced bag/meter profile, and effects a strong bond between the meter and the bag.

SUMMARY

In accordance with the present disclosure, a urine meter is provided which includes a housing and a substantially transparent faceplate. The housing defines an inlet port and includes an upper wall, a lower wall, sidewalls, and a rear wall. In one embodiment, the upper wall of the housing is substantially concave and includes a central portion and first and second ends. The central portion has a height which is less than the height of the first and second ends of the upper wall. The housing also defines at least one drain opening. In one embodiment, first and second drain openings are provided. The first and second drain openings are positioned adjacent the first and second ends of the upper wall. A recessed channel can be formed at least partially about the first and second drain openings to improve drainage.

In one embodiment, the at least one fluid receptacle includes first and second receptacles. The first fluid receptacle is centrally located within the housing to receive fluid from the inlet port. The second fluid receptacle includes a left receptacle portion positioned on one side of the first receptacle and a right receptacle portion positioned on an opposite side of the first receptacle. The left and right receptacle portions are interconnected by a fluid channel. In one embodiment, the fluid channel extends beneath the first receptacle.

The urine meter can include a drain tube having a discharge end which extends or is positioned through the inlet port. The drain tube includes a smooth internal surface having substantially no discontinuities. In one embodiment, the discharge end of the drain tube is angled or tapered.

In one embodiment, a needleless sampling port is provided to access fluid in the first receptacle. The sampling port can be supported on the faceplate such that upon attachment of the faceplate to the housing, the sampling port is in fluid communication with the first receptacle. The faceplate can include indicia for identifying the volume of fluid within the first and second fluid receptacles. One or more sets of indicia may be provided to indicate the volume of fluid in each or all of the housing receptacles.

A method for securing a urine meter to a urine collection bag is also disclosed. The method includes the steps of providing a meter including a housing defining at least one fluid receptacle and at least one drain opening positioned at an upper end of the housing; providing a collection bag defining a fluid reservoir and having at least one inlet opening; positioning the meter adjacent to the collection bag such that the at least one drain opening is positioned in fluid communication with the at least one inlet opening; and using an RF welding device to secure the meter to the collection bag such that the at least one fluid receptacle is in fluid communication with the fluid reservoir via the at least one drain opening and the at least one inlet opening. In one embodiment, the step of providing a meter includes the step of providing a raised surface on the housing of the meter which is positioned about the at least one drain opening, and the step of using an RF welding device includes the step of welding the collection bag to the raised surface of the housing of the meter. The at least one drain opening can include two drain openings and the at least one inlet opening can include two inlet openings. In one embodiment, the meter is constructed from a polyester terephthalate modified with glycol ("PETG") and the collection bag is formed from polyvinyl chloride.

BRIEF DESCRIPTION OF THE DRAWINGS

Various embodiments of the presently disclosed urine meter and collection bag assembly are disclosed herein with reference to the drawings, wherein.

DETAILED DESCRIPTION OF EMBODIMENTS

Embodiments of the presently disclosed urine meter and collection bag assembly will now be described in detail with reference to the drawings wherein like reference numerals designate identical or corresponding elements in each of the several views.

Figure 1:
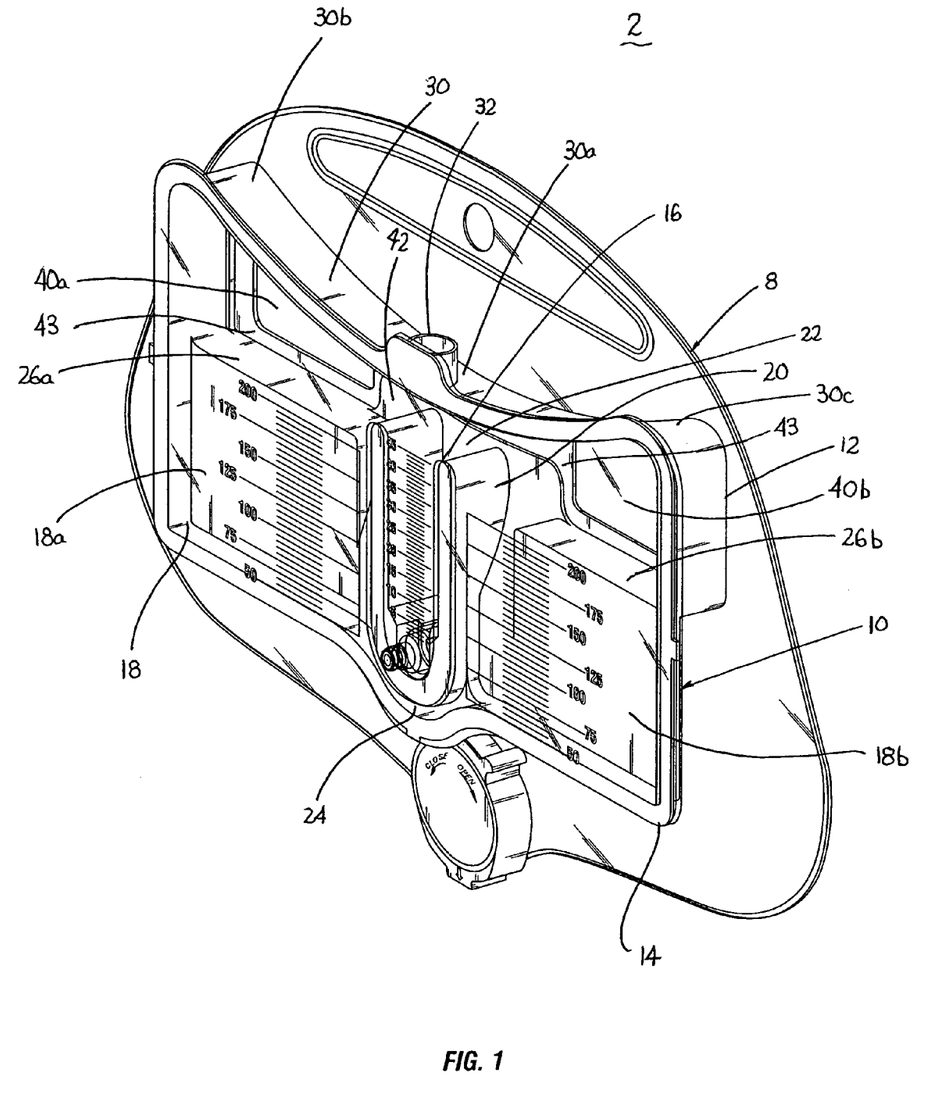
FIG. 1 is a side perspective view of one embodiment of the presently disclosed urine meter and collection bag assembly.
Figure 2:
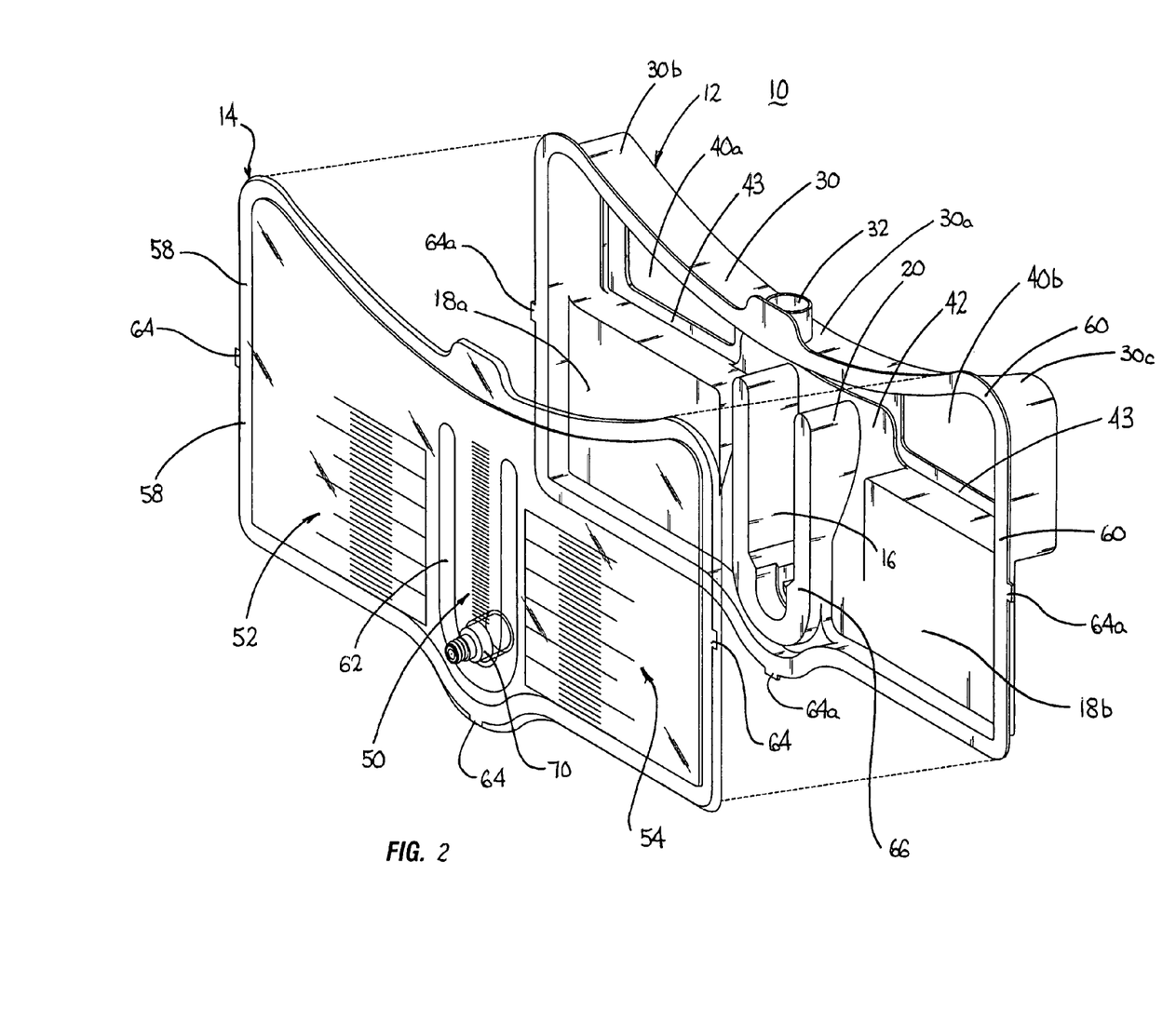
FIG. 2 is a side perspective view of the urine meter shown in FIG. 1 with the faceplate of the urine meter separated from the housing.
Figure 3:
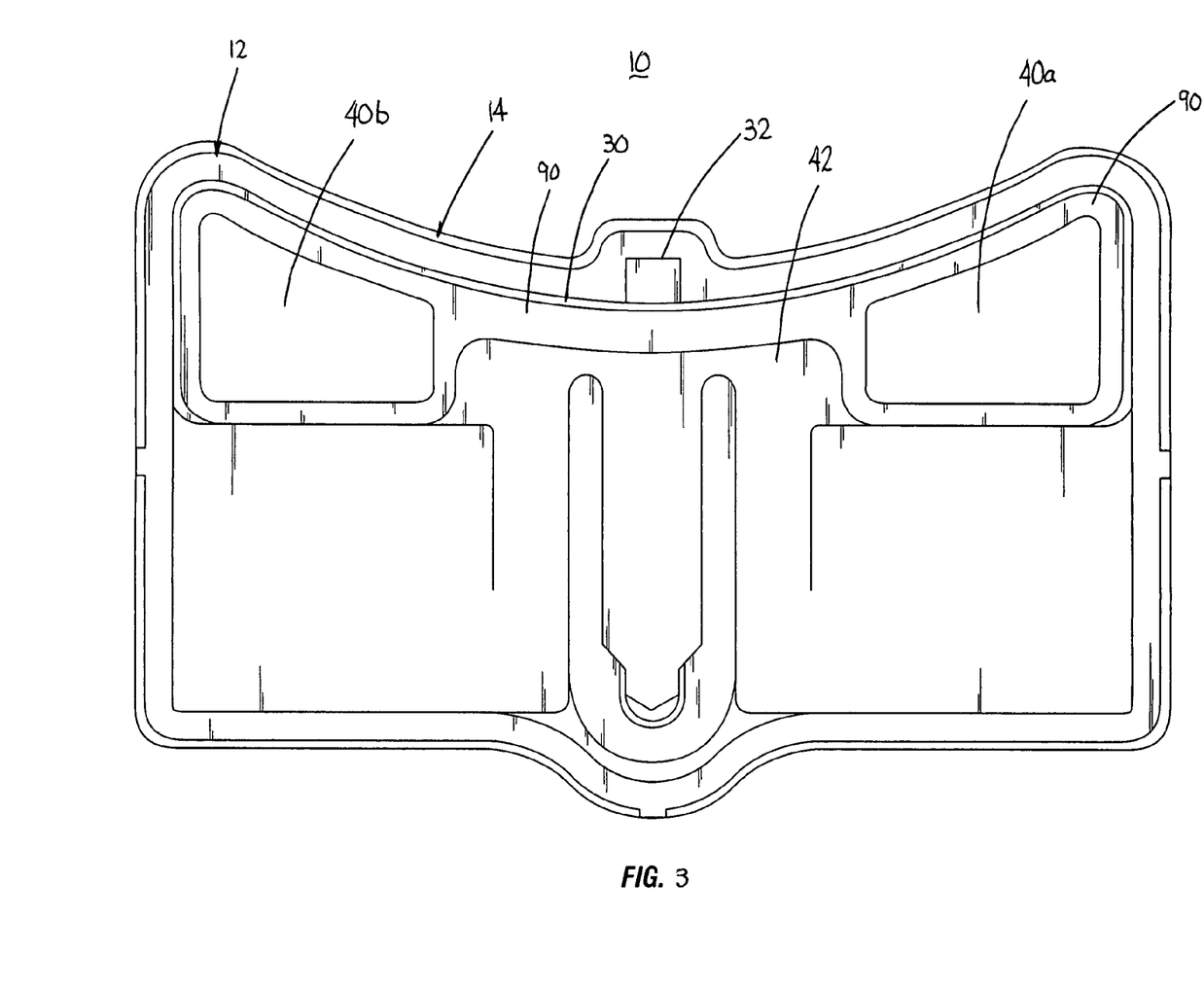
FIG. 3 is a rear view of the urine meter shown in FIG. 2.
Figure 4:
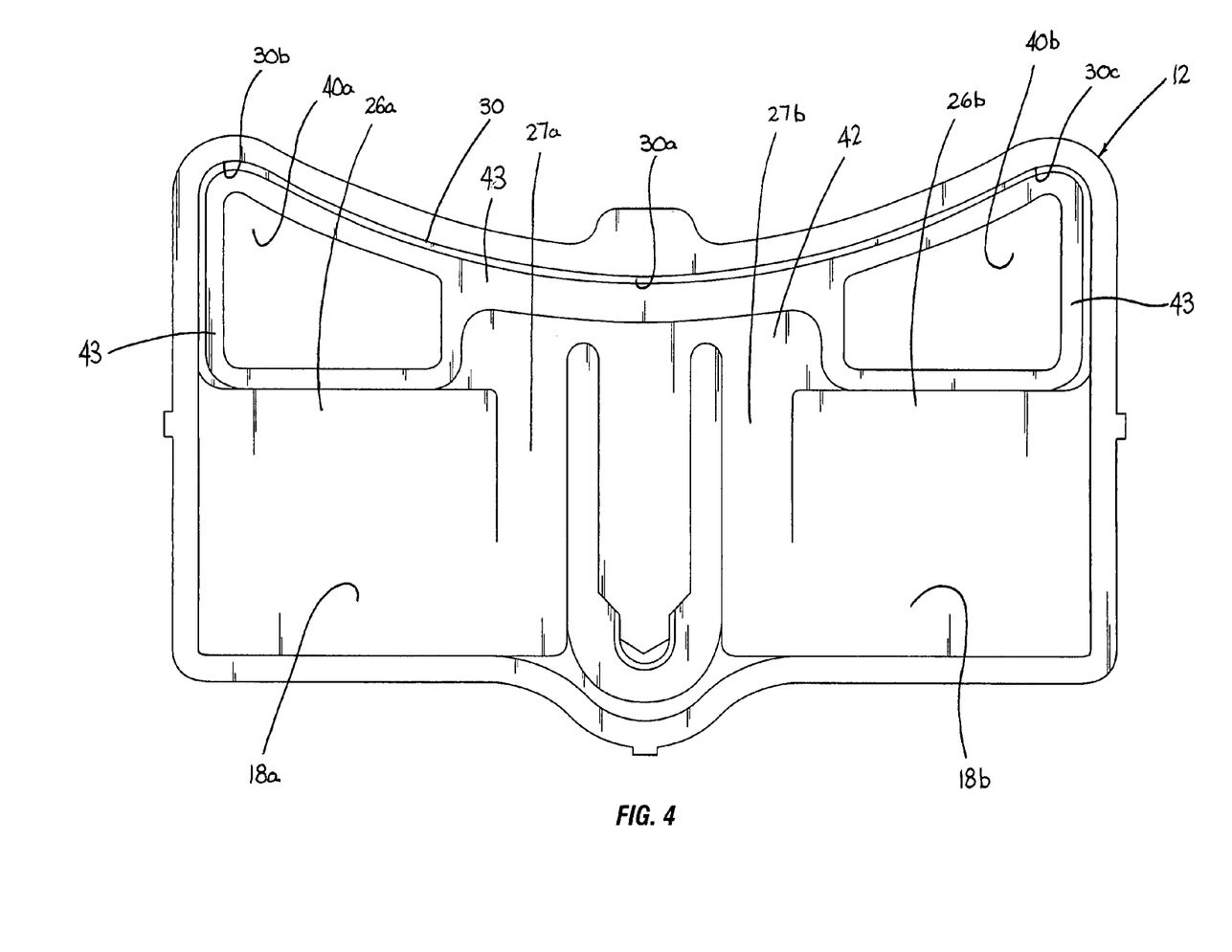
FIG. 4 is a front view of the urine meter housing shown in FIG. 2.

FIG. 1 illustrates one embodiment of the presently disclosed urine meter and collection bag assembly which is shown generally as 2 and includes a collection bag 8 and a urine meter 10. Referring also to FIGS. 2-4, urine meter 10 includes a housing 12 and a faceplate 14. Housing 12 and faceplate 14 can be constructed from a polyester terephalate modified with glycol ("PETG"). PETG is a substantially rigid, transparent material. In one embodiment, housing 12 and faceplate 14 are injection molded. Alternatively, other materials having similar characteristics can be used to construct housing 12 and faceplate 14. In one embodiment, housing 12 has a width which is greater than its height and defines a first receptacle 16 and a second receptacle 18. It is envisioned that one or more, e.g., 3 or 4, fluid receptacles can be provided within housing 12. First receptacle 16 is centrally located within housing 12 and is dimensioned and configured to receive small volumes of urine. As illustrated, first receptacle 16 may be dimensioned to receive about 45 ml of fluid. Alternately, the dimensions of first receptacle 16 may be varied to hold different volumes of fluid, e.g., 10-100 ml. In one embodiment, first receptacle 16 is defined by a substantially U-shaped wall 20 which can be formed integrally or monolithically with housing 12. Alternately, other wall or receptacle configurations are envisioned, e.g., rectangular, etc. The upper end of receptacle 16 defines an opening 22 dimensioned to receive fluid flow, as will be discussed in further detail below, and allow fluid to spillover from first receptacle 16 into second receptacle 18.

Second receptacle 18 is positioned about first receptacle 16 and includes a left receptacle portion 18a and a right receptacle portion 18b. Left and right receptacle portions 18a and 18b are positioned on opposite sides of receptacle 16 and communicate with each other via a fluid channel 24 extending beneath first receptacle 16. Fluid channel 24 allows the pressure and thus the level of fluid in receptacle portions 18a and 18b to become balanced even though a greater volume of fluid may spillover from first receptacle 16 into one or the other of the left and right receptacle portions 18a and 18b. It is envisioned that where three or more fluid receptacles are provided in housing 12, the additional fluid receptacles would each include two receptacle portions located outwardly and on opposite sides of the first and second receptacles and joined by a fluid channel.

Housing 12 includes stepped portions 26a and 26b which define the rear walls of left and right receptacle portions 18a and 18b, respectively. Stepped portions 26a and 26b are positioned adjacent indicia on faceplate 14 and reduce the depth of receptacle portions 18a and 18b within housing 12 to thereby reduce the volume of receptacle portions 18a and 18b. By reducing the volume of receptacle portions 18a and 18b in this manner in conjunction with providing a second receptacle 18 positioned about a centrally located first receptacle 16, smaller volumes of fluid are more readily apparent in second receptacle 18. Thus, greater spacing can be provided between indicia provided on faceplate 14 to allow more accurate measurement of small volumes of fluid in second receptacle 18.

In one embodiment, housing 12 also defines sloped or angled surfaces 27a and 27b (FIG. 4) positioned between stepped portions 26a and 26b, respectively and opposite sides of wall 20. Sloped surfaces 27a and 27b define a sloped surface which extends from a front face of stepped portions 26a and 26b, respectively, towards a rear wall 42 of housing 12. Sloped surfaces 27a and 27b allow fluid to flow from receptacle portions 18a and 18b towards drain openings 40a and 40b as will be discussed in further detail below.

The upper portion of housing 12 is defined by an upper wall 30 having a substantially concave configuration. Upper wall 30 has a central portion 30a defining a low point of the concavity and opposite ends 30b and 30c which are positioned above central portion 30a. An inlet port 32 which can be integrally or monolithically formed with housing 12 extends through central portion 30a of upper wall 30. Inlet port 32 is positioned to enter urine meter 10 at the lowest point of upper wall 30 to improve the flow of fluid from a patient into the urine meter, i.e., by lowering the inlet height of fluid entry into meter 10 in a gravity feed system, the differential height between the inlet and outlet ends of a drain tube is increased to increase the head pressure of the fluid in the drain tube. In one embodiment, upperwall 30 defines smoothly, curved inner surface. Alternately, upper wall 30 can have a variety of different concave configurations in which a central portion of upper wall 30 defines a low point of the upper wall. For example, upper wall 30 can include a pair of linear wall portions which converge downwardly towards each other and meet at a central portion of the upper wall.

Housing 12 also defines a pair of spaced drain openings 40a and 40b which are positioned above receptacle portions 18a and 18b, respectively. Drain openings 40a and 40b are defined in opposite sides of a rear wall 42 of housing 12 and are located beneath ends 30b and 30c of upper wall 30 of housing 12 such that openings 40a and 40b extend to a position adjacent the upper most portions of housing 12. A recessed channel or groove 43 is positioned around drain openings 40a, along upper wall 30 and around drain opening 40b. Alternately, channel 43 can extends only partially about one or both of the drain openings. Groove 43 functions enhance drainage of urine meter 10. In one embodiment, drain openings 40a and 40b each define a substantial portion of the overall surface area of the upper portion of rear wall 42 of housing 12. Because of the area of openings 40a and 40b, their location in the uppermost corner of the concave upper wall 30, the provision of a groove about drain openings 40a and 40b, and sloped walls 27a and 27b, fluid can be emptied from urine meter quickly and completely. It is envisioned that any one or any combination of these features can be incorporated into a urine meter to improve drainage of the urine meter.

Referring to FIG. 2, faceplate 14 is substantially transparent and includes a first set of indicia 50 positioned adjacent first receptacle 16, a second set of indicia 52 positioned adjacent first receptacle portion 18a and a third set of indicia 54 positioned adjacent second receptacle portion 18b. Indicia 52 is substantially identical to indicia 54. Faceplate 14 includes an outer rim 58 which is positioned to abut an outer rim 60 positioned about a forward portion of housing 12. Rims 58 and 60 are secured together in a fluid tight manner to seal faceplate 14 to housing 12. In one embodiment, faceplate 14 is secured to housing 12 using radio frequency ("RF") welding. Alternately, other known fastening techniques can be used to secure faceplate 14 to housing 12, e.g., adhesives, clamps, screws, ultrasonic welding etc.

A central portion of faceplate 14 includes a seal portion 62 which is configured to abut a face 66 of wall 20 defining first receptacle 16. Seal portion 62 is secured to wall 20 in a fluid tight manner, e.g., welding, adhesives, etc. to seal first receptacle 16 from second receptacle 18. A series of positioning tabs 64 are positioned about rim 58 of faceplate 14. Positioning tabs 64 align with tabs or slots 64a formed on rim 60 of housing 12 to properly position faceplate 14 in relation to housing 12 during attachment of faceplate 14 to housing 12.

Faceplate 14 also includes a sampling port 70 which is positioned to provide access to fluid in the bottom of receptacle 16. Sampling port 70 is configured to access first receptacle 16 using either a luer-loc or slip tip syringe. Such a valve is available from NP Medical, Inc., a division of Nypro, Inc., of Clinton, Ma. Sampling port 70 eliminates a potential site for bacterial entrance into urine meter 10, while decreasing the likelihood of human contact with urine.

As discussed above, inlet port 32 is dimensioned to receive a drain tube (not shown). The first end of the drain tube is adapted to be in fluid communication with a catheterized patient such that urine from a patient's bladder flows via gravity from the patient's bladder and is initially collected in urine meter 10. The second end of the drain tube extends directly through inlet port 32 to a position above first receptacle 16.

Referring to FIG. 3, the back side 100 of housing 12 of urine meter 10 includes a raised surface 90 which extends about drain openings 40a and 40b and along rear wall 42 adjacent upper wall 30. Raised surface 90 is positioned to engage urine collection bag 8 and be sealed in a fluid tight manner thereto as will be described in further detail below.

Figure 5:
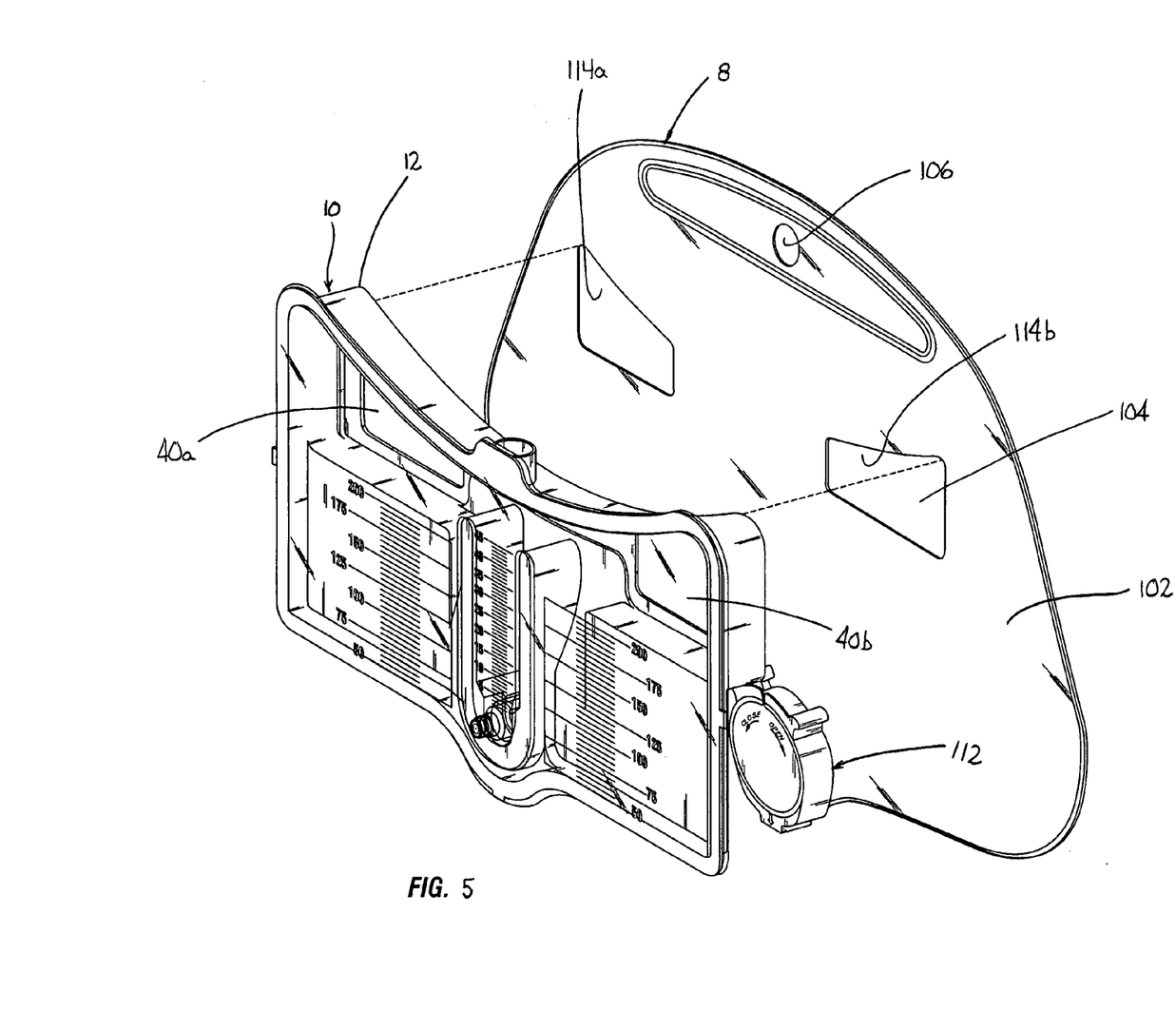
FIG. 5 is a side perspective view of the urine meter and collection bag shown in FIG. 1 prior to securement of the urine meter to the collection bag.

Referring to FIG. 5, collection bag 8 is formed from a flexible material and defines a fluid reservoir for receiving fluid from urine meter 10. In one embodiment, bag 8 is formed from front and rear sheets 102 and 104 of a polymeric material, e.g., polyvinylchloride (PVC), which are joined together at their edges such as by RF or ultrasonic welding to define a fluid reservoir. Alternately, front and rear sheets 102 and 104 may be joined together using any known sealing process including heat sealing or the like.

In one embodiment, an upper portion of bag 8 includes an opening 106 which is dimensioned to receive a support member, e.g., a hangar or hook, for supporting the urine meter and collection bag assembly on a support surface, e.g., a hospital bed frame. Sheets 102 and 104 of bag 8 may be joined together in the area 108 positioned about opening 106 to provide increased strength to bag 8 at the support location.

Figure 6:
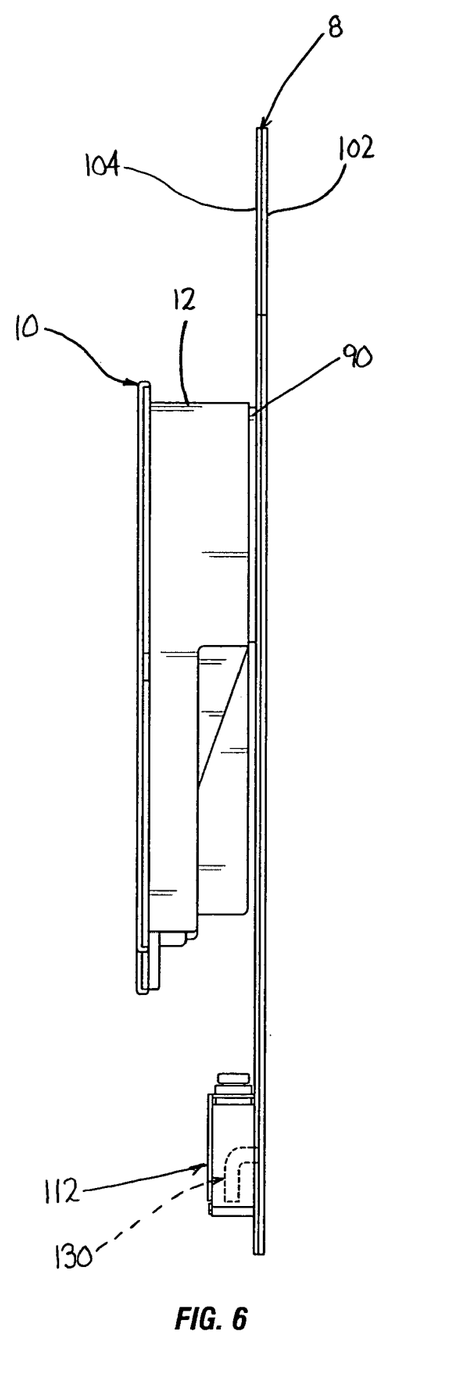
FIG. 6 is a side view of the urine meter and collection bag assembly shown in FIG. 1.
Figure 7:
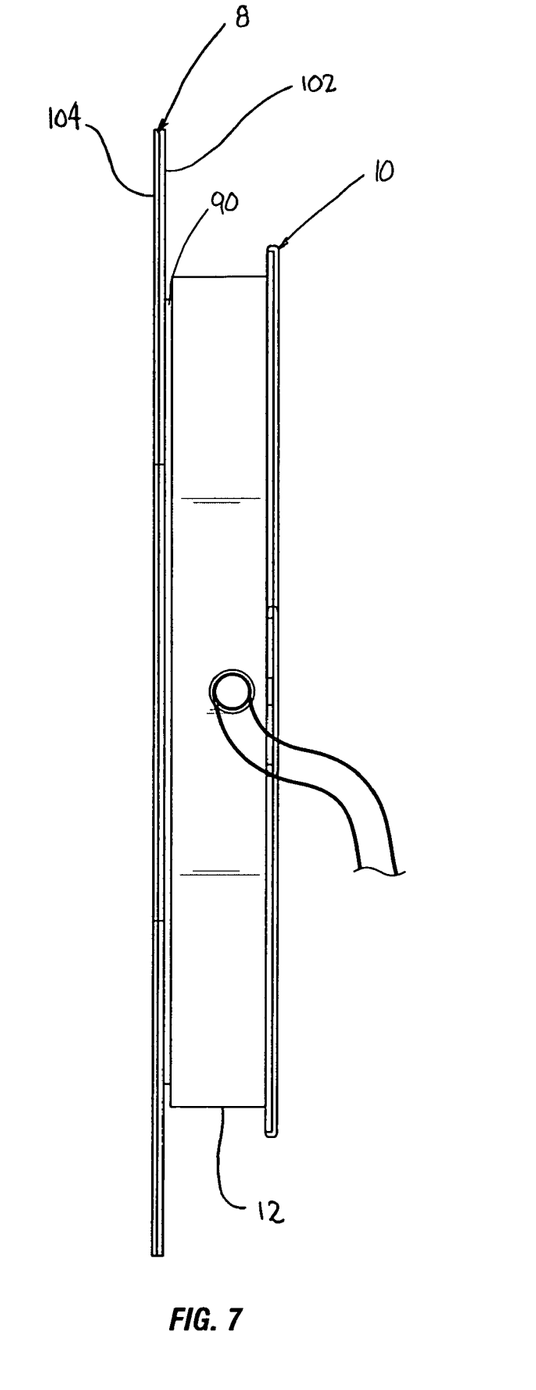
FIG. 7 is a top view of the urine meter and collection bag assembly shown in FIG. 1.

In one embodiment, a gully or recess 110 is provided at a bottom of bag 8. A discharge opening (not shown) which communicates with a discharge tube 130 (FIG. 6) extends into a discharge valve 112. Discharge valve 112 is operable to effect drainage of collection bag 8.

Front sheet 102 of bag 8 includes openings 114a and 114b which correspond in shape and size to openings 40a and 40b of urine meter housing 12 (FIG. 3). Openings 114a and 114b communicate with openings 40a and 40b to allow urine meter 10 to drain into collection bag 8.

As discussed above, a raised surface 90 is positioned on rear wall 42 of urine meter housing 12. Raised surface 90 extends around drain openings 40a and 40b of housing 12 and is positioned to abut front sheet 102 of collection bag 8. In one method of forming the urine meter and collection bag assembly, raised surface 90 of housing 12 is positioned to abut front sheet 102 of collection bag 8 about openings 114a and 114b. Next, raised surface 90 is sealingly attached to front sheet 102 using a Radio Frequency ("RF") welding device. Raised surface 90 allows for the use of such a fastening process. The RF welding process is inexpensive, results in a strong bond between the meter and the collection bag and provides a meter/bag assembly having a lower profile, i.e, obviates the need for docking structure.

It will be understood that various modifications may be made to the embodiments disclosed herein. For example, additional walls or barriers may be provided to divide meter 10 into additional receptacles, e.g., a third or receptacle may be provided by providing an additional wall or walls in left and right receptacle portions 18a and 18b. Further, the configuration of the meter and bag need not be as disclosed to achieve the benefits of the method of attachment. Accordingly, other bag and meter configurations are envisioned. Therefore, the above description should not be construed as limiting, but merely as exemplifications of preferred embodiments. Those skilled in the art will envision other modifications within the scope and spirit of the claims appended hereto.

What is claimed is:

1. A method for securing a urine meter to a urine collection bag, wherein the method comprises the following steps:
   providing a meter including a housing defining at least one fluid receptacle and at least one drain opening positioned at an upper end of the housing;
   providing a collection bag defining a fluid reservoir, the collection bag including at least one inlet opening;
   positioning the meter adjacent to the collection bag such that the at least one drain opening is positioned in fluid communication with the at least one inlet opening; and
   using an RF welding device to secure the meter to the collection bag such that the at least one fluid receptacle is in fluid communication with the fluid reservoir via the at least one drain opening and the at least one inlet opening, and
   wherein the meter is constructed from a polyester terephthalate modified with glycol ("PETG").

2. A method according to claim 1, wherein the step of providing a meter includes the step of providing a raised surface on the housing of the meter which is positioned about the at least one drain opening, and the step of using an RF welding device includes the step of welding the collection bag to the raised surface of the housing of the meter.

3. A method according to claim 1, wherein the at least one drain opening includes two drain openings and the at least one inlet opening includes two inlet openings.

4. A method according to claim 2, wherein the meter is constructed from a polyester terephthalate modified with glycol ("PETG") and the collection bag is formed from polyvinyl chloride.

5. A method according to claim 3, wherein the two drain openings are positioned on opposite sides of the meter and the raised surface on the housing extends about a first of the two drain openings, along an upper portion of the housing of the meter, and about a second of the two drain openings.

6. A method according to claim 1, wherein the housing of the meter is injection molded.

7. A method according to claim 6, wherein the housing is formed from a polyester terephthalate modified with glycol ("PETG") and the collection bag is formed from polyvinyl chloride.

8. A method according to claim 2, wherein the housing of the meter is injection molded.

9. A method according to claim 8, wherein the housing is formed from a polyester terephthalate modified with glycol ("PETG") and the collection bag is formed from polyvinyl chloride.

10. A method according to claim 1, wherein the collection bag is formed from polyvinyl chloride.

* * * * *